(12) United States Patent
Yin et al.

(10) Patent No.: US 8,852,619 B2
(45) Date of Patent: Oct. 7, 2014

(54) COMPOSITIONS OF DIBROMOMALONAMIDE AND THEIR USE AS BIOCIDES

(75) Inventors: Bei Yin, Buffalo Grove, IL (US); Charles D. Gartner, Midland, MI (US); Freddie L. Singleton, Vernon Hills, IL (US)

(73) Assignee: Dow Global Technologies LLC, Midland, MI (US)

( * ) Notice: Subject to any disclaimer, the term of this patent is extended or adjusted under 35 U.S.C. 154(b) by 2 days.

(21) Appl. No.: 13/391,908

(22) PCT Filed: Sep. 27, 2010

(86) PCT No.: PCT/US2010/050349
§ 371 (c)(1),
(2), (4) Date: Feb. 23, 2012

(87) PCT Pub. No.: WO2011/038321
PCT Pub. Date: Mar. 31, 2011

(65) Prior Publication Data
US 2012/0172430 A1    Jul. 5, 2012

Related U.S. Application Data

(60) Provisional application No. 61/246,191, filed on Sep. 28, 2009.

(51) Int. Cl.
*A01N 37/34*    (2006.01)
*A01P 1/00*    (2006.01)
*C02F 1/50*    (2006.01)
*A01N 37/30*    (2006.01)
*A01N 37/40*    (2006.01)

(52) U.S. Cl.
CPC . *A01N 37/30* (2013.01); *C02F 1/50* (2013.01); *A01N 37/40* (2013.01)
USPC .......................................... 424/405; 514/528

(58) Field of Classification Search
CPC ... A01N 37/40; A01N 2300/00; A01N 37/30; A01N 37/34; C02F 1/50
USPC .......................................... 514/528; 424/405
See application file for complete search history.

(56) References Cited

U.S. PATENT DOCUMENTS

| | | | |
|---|---|---|---|
| 3,647,610 A * | 3/1972 | Wolf | 162/161 |
| 4,241,080 A | 12/1980 | Burk | |
| 4,732,913 A | 3/1988 | Donofrio et al. | |
| 4,800,082 A * | 1/1989 | Karbowski et al. | 424/409 |
| 5,723,486 A | 3/1998 | Wu et al. | |
| 2004/0261196 A1 | 12/2004 | Ghosh et al. | |
| 2010/0096326 A1* | 4/2010 | Najmy et al. | 210/636 |

FOREIGN PATENT DOCUMENTS

| JP | 10-067608 A | 3/1998 |
|---|---|---|
| WO | 2008/091453 A1 | 7/2008 |

OTHER PUBLICATIONS

J. H. Exner, et al., Rates and Products of Decomposition of 2,2-Dibromo-3-nitrilopropionamide, Journal of Agricultural and Food Chemistry, 1973, pp. 838-842, vol. 21, Issue 5.

* cited by examiner

*Primary Examiner* — Janet Epps-Smith
*Assistant Examiner* — Courtney Brown
(74) *Attorney, Agent, or Firm* — Tifani M. Edwards

(57) ABSTRACT

A biocidal composition comprising 2,2-dibromomalonamide and 2,2-dibromo-3-nitrilopropionamide, and its use for the control of microorganisms in aqueous and water-containing systems.

5 Claims, No Drawings

COMPOSITIONS OF DIBROMOMALONAMIDE AND THEIR USE AS BIOCIDES

CROSS REFERENCE TO RELATED APPLICATIONS

This application is a 35 USC §371 national phase filing of PCT/US2010/050349 filed Sep. 27, 2010, which claims the benefit of U.S. Application No. 61/246,191, filed Sep. 28, 2009.

FIELD OF THE INVENTION

The invention relates to a biocidal composition and methods of its use for the control of microorganisms in aqueous and water-containing systems. The composition comprises 2,2-dibromomalonamide and 2,2-dibromo-3-nitrilopropionamide.

BACKGROUND OF THE INVENTION

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and 2,2-dibromo-3-nitrilopropionamide.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and 2,2-dibromo-3-nitrilopropionamide. It has surprisingly been discovered that combinations of 2,2-dibromomalonamide and 2,2-dibromo-3-nitrilopropionamide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

In addition to the overall effectiveness against microorganisms in aqueous and water containing systems, the combination of 2,2-dibromomalonamide and 2,2-dibromo-3-nitrilopropionamide according to the invention is also more resistant to hydrolysis at near-neutral-to-alkaline pH than the 2,2-dibromo-3-nitrilopropionamide component when acting alone. Thus, whereas 2,2-dibromo-3-nitrilopropionamide is stable under acidic conditions, it is known to undergo rapid hydrolytic degradation in neutral to basic solution. Its rate of disappearance increases by a factor of about 450 in going from pH 6, essentially neutral, to pH 8.9, slightly basic. See, Exner et al., *J. Agr. Food. Chem.*, 1973, 21(5), 838-842 ("Exner"). At pH 8, the half life for 2,2-dibromo-3-nitrilopropionamide is 2 hours. (Exner, Table 1). At pH 11.3, the half life is only 25 sec, essentially instantaneous degradation. (Exner, page 839, left column). 2,2-Dibromo-3-nitrilopropionamide, therefore, is seldom an attractive biocide for prolonged microbial control in alkaline water systems.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation.

The term "2,2-dibromomalonamide" refers to a compound represented by the following chemical formula:

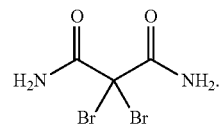

The 2,2-dibromomalonamide of the composition of the invention is commercially available. 2,2-Dibromo-3-nitrilopropionamide is also commercially available, for instance from The Dow Chemical Company. Both materials can also be readily prepared by those skilled in the art using well known techniques.

In some embodiments, the weight ratio of 2,2-dibromomalonamide to 2,2-dibromo-3-nitrilopropionamide in the composition of the invention is between about 100:1 and about 1:20.

In some embodiments, the weight ratio of 2,2-dibromomalonamide to 2,2-dibromo-3-nitrilopropionamide is between about 70:1 and about 1:10.

In some embodiments, the weight ratio of 2,2-dibromomalonamide to 2,2-dibromo-3-nitrilopropionamide is between about 40:1 and about 1:5.

In some embodiments the weight ratio of 2,2-dibromomalonamide to 2,2-dibromo-3-nitrilopropionamide is between about 31:1 and about 1:1.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries, polymer emulsions, caulks and adhesives, tape joint compounds, disinfectants, sanitizers, metalworking fluids, construction products, personal care products, textile fluids such as spin finishes, industrial process water (e.g., oilfield water, pulp and paper water, cooling water), oilfield functional fluids such as drilling muds and fracturing fluids, and fuels. Preferred aqueous systems are detergents, personal care, household, and industrial products, paints/coatings, and industrial process water. Particularly preferred are metal working fluids, mineral slurries, polymer emulsions, and industrial process water.

In some embodiments of the invention, the aqueous or water containing system to be treated has a pH of 5 or greater. In preferred embodiments, the pH is 7 or greater. In further preferred embodiments, the pH is 8 or greater.

A person of ordinary skill in the art can readily determine, without undue experimentation, the effective amount of the composition that should be used in any particular application to provide microorganism control. By way of illustration, a suitable actives concentration (total for both 2,2-dibromomalonamide and 2,2-dibromomalonamide and 2,2-dibromo-3-nitrilopropionamide) is typically at least about 1 ppm, alternatively at least about 3 ppm, alternatively at least about 7 ppm, alternatively at least about 10 ppm, or alternatively at least about 100 ppm based on the total weight of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the total weight of the aqueous or water containing system.

The components of the composition can be added to the aqueous or water containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

Example 1

Evaluation of DBMAL, DBNPA, and Combinations Using a Growth Inhibition Assay

The assay of this Example measures the efficacy of the biocides at preventing growth of a consortium of bacteria in a dilute mineral salts medium. The medium contains (in mg/l) the following components: $FeCl_3 \cdot 6H_2O$ (1); $CaCl_2 \cdot 2H_2O$ (10); $MgSO_4 \cdot 7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 ul quantities to sterile microtiter plate wells. Dilutions of 2,2-dibromomalonamide ("DBMAL") and/or "Biocide B" are then added to the microtiter plate. After preparing the combinations of actives as illustrated below, each well is inoculated with 100 μl of a cell suspension containing ca. $1 \times 10^6$ cells per milliliter of a mixture of *Pseudomonas aeruginosa*, *Klebsiella pneumoniae*, *Staphylococcus aureus*, and *Bacillus subtilis*. The final total volume of medium in each well is 300 μl. Once prepared as described herein, the concentration of each active ranges from 25 ppm to 0.195 ppm as illustrated in Table 1. The resulting matrix allows testing of eight concentrations of each active and 64 combinations of actives at varying ratios.

TABLE 1

Template for microtiter plate-based synergy assay showing concentrations of each active. Ratios are based on weight (mg/l, nominally ppm) of each active.

|  |  | DBMAL (ppm) | | | | | | | |
| --- | --- | --- | --- | --- | --- | --- | --- | --- | --- |
|  |  | 25.000 | 12.500 | 6.250 | 3.125 | 1.563 | 0.781 | 0.391 | 0.195 |
| Biocide DBNPA (ppm) | 25.000 | 1:1 | 1:2 | 1:4 | 1:8 | 1:16 | 1:32 | 1:64 | 1:128 |
|  | 12.500 | 2:1 | 1 | 1:2 | 1:4 | 1:8 | 1:16 | 1:32 | 1:64 |
|  | 6.250 | 4:1 | 2:1 | 1 | 1:2 | 1:4 | 1:8 | 1:16 | 1:32 |
|  | 3.125 | 8:1 | 4:1 | 2:1 | 1 | 1:2 | 1:4 | 1:8 | 1:16 |
|  | 1.563 | 16:1 | 8:1 | 4:1 | 2:1 | 1 | 1:2 | 1:4 | 1:8 |
|  | 0.781 | 32:1 | 16:1 | 8:1 | 4:1 | 2:1 | 1 | 1:2 | 1:4 |
|  | 0.391 | 64:1 | 32:1 | 16:1 | 8:1 | 4:1 | 2:1 | 1 | 1:2 |
|  | 0.195 | 128:1 | 64:1 | 32:1 | 16:1 | 8:1 | 4:1 | 2:1 | 1:1 |

Controls (not shown) contain the medium with no biocide added. Immediately after the microtiter plates are prepared, the optical density (OD) readings for each well are measured at 600 nm and the plates are then incubated at 37° C. for 24 hr. After the incubation period, the plates are gently agitated before OD values are collected. The OD values at t(0) are subtracted from t(24) values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

$$\text{Synergy Index} = M_{DBMAL}/C_{DBMAL} + M_{DBNPA}/C_{DBNPA}$$

where
$M_{DBMAL}$: Concentration of DBMAL required to inhibit ~90% of bacterial growth when used in combination with DBNPA.
$C_{DBMAL}$: Concentration of DBMAL required to inhibit ~90% of bacterial growth when used alone.
$M_{DBNPA}$: Concentration of DBNPA required to inhibit ~90% of bacterial growth when used in combination with DBMAL.
$C_{DBNPA}$: Concentration of DBNPA required to inhibit ~90% of bacterial growth when used alone.

The SI values are interpreted as follows:
SI<1: Synergistic combination
SI=1: Additive combination
SI>1: Antagonistic combination In the Example, the amounts of biocides in the solution are measured in mg per liter of solution (mg/l). Since solution densities are approximately 1.00, the mg/l measurement corresponds to weight ppm. Both units may therefore be used interchangeably in the Examples.

Table 2 shows inhibition growth assay results for DBMAL, 2,2-dibromo-3-nitrilopropionamide ("DNBPA"), and combinations thereof. The minimum concentrations of DBMAL and DBNPA that caused ~90% inhibition of growth are 12.5 ppm ($C_{DBMAL}$) and 3.13 mg/l ($C_{DBNPA}$), respectively.

Example 2

Evaluation of DBMAL, DBNPA, and Combinations Using a Kill Assay

This Example demonstrates the ability of the composition of the invention to provide rapid kill and long term microorganism control when used in an aqueous system at elevated pH.

Sterile artificial Cooling Tower water (0.2203 g of $CaCl_2$, 0.1847 g of $MgSO_4$, and 0.2033 g of $NaHCO_3$ in 1 L water, approximately pH 8.5) is contaminated with *Pseudomonas aeruginosa* ATCC 10145 at approximately $10^{6-7}$ CFU/mL. The aliquots of this contaminated water are then treated with DBMAL, DBNPA, or their combinations. After incubating at 30° C. for 1 hr, 3 hrs, 24 hrs, and 48 hrs, the valid bacteria in the aliquots are enumerated using a serial dilution technique. All aliquots are re-challenged daily with *P. aeruginosa* ATCC 10145 at approximately $10^{5-6}$ CFU/mL. Table 4 summarizes the log kill of DBMAL, DBNPA, and each DBNPA/DBMAL combination at 9.9 ppm active dosage level during the 1 hour to 48 hours contact time period. Various combinations show both fast kill (3 hr) and long lasting efficacy (24 hours and 48 hours) compared to DBNPA and DBMAL alone.

TABLE 2

Percent inhibition of growth, as measured by changes in optical density values (600 nm), in a bacterial consortium challenged with DBMAL, DBNPA, and combinations of these actives.

| | | DBMAL (ppm) | | | | | | | | DBMAL alone | DBNPA alone | Control | Blank |
|---|---|---|---|---|---|---|---|---|---|---|---|---|---|
| | | 25 | 12.5 | 6.25 | 3.12 | 1.56 | 0.78 | 0.39 | 0.19 | | | | |
| DBNPA (ppm) | 25.00 | 100 | 99 | 96 | 92 | 98 | 99 | 98 | 99 | 96 | 96 | 0 | 0 |
| | 12.50 | 99 | 98 | 95 | 98 | 98 | 99 | 98 | 85 | 92 | 88 | 42 | 0 |
| | 6.25 | 99 | 98 | 96 | 97 | 98 | 98 | 73 | 94 | 38 | 82 | 23 | 0 |
| | 3.13 | 99 | 96 | 98 | 95 | 86 | 92 | 0 | 0 | 0 | 98 | 0 | 0 |
| | 1.56 | 98 | 99 | 97 | 99 | 87 | 9 | 0 | 0 | 11 | 75 | 0 | 0 |
| | 0.78 | 100 | 98 | 96 | 98 | 98 | 0 | 0 | 0 | 0 | 0 | 0 | 0 |
| | 0.39 | 100 | 99 | 98 | 88 | 89 | 0 | 0 | 0 | 0 | 0 | 0 | 0 |
| | 0.20 | 100 | 98 | 96 | 98 | 83 | 0 | 0 | 0 | 0 | 0 | 0 | 0 |

Table 3 shows ratios of DBMAL and DBNPA found to be synergistic under the growth inhibition assay. The data demonstrates that synergy is observed at ratios ranging from 31:1 to 1:1 (DBMAL:DBNPA)

TABLE 3

| DBMAL (mg/l) | DBNPA (mg/l) | Ratio (DBMAL to DBNPA) | SI |
|---|---|---|---|
| 1.56 | 1.56 | 1:1 | 0.6 |
| 1.56 | 0.78 | 2:1 | 0.4 |
| 1.56 | 0.39 | 4:1 | 0.2 |
| 3.12 | 1.56 | 2:1 | 0.7 |
| 3.12 | 0.78 | 4:1 | 0.5 |
| 3.12 | 0.39 | 8:1 | 0.4 |
| 3.12 | 0.2 | 16:1 | 0.3 |
| 6.25 | 0.78 | 8:1 | 0.7 |
| 6.25 | 0.39 | 16:1 | 0.6 |
| 6.25 | 0.2 | 31:1 | 0.6 |

TABLE 4

Log kill of DBMAL, DBNPA, and each DBNPA/DBMAL combination

| DBNPA:DBMAL (active weight ratio) | Bacterial log reduction at differenat time intervals after the addition of biocide (9.9 ppm, active) | | | |
|---|---|---|---|---|
| | 1 hr | 3 hr | 24 hr | 48 hr |
| DBNPA alone | 3.67 | 6.30 | 5.30 | 1.00 |
| DBMAL alone | 2.00 | 3.00 | 5.00 | 5.00 |
| 10:1 | 4.67 | 6.30 | 5.30 | 1.00 |
| 8:1 | 4.67 | 6.30 | 5.30 | 1.67 |
| 4:1 | 2.00 | 6.30 | 5.30 | 0.67 |
| 2:1 | 2.00 | 6.30 | 5.30 | 0.67 |
| 1:1 | 1.67 | 6.30 | 5.00 | 5.70 |
| 1:2 | 1.00 | 6.30 | 5.30 | 4.67 |
| 1:4 | 0.33 | 6.30 | 5.30 | 3.34 |
| 1:8 | 0.33 | 4.66 | 5.30 | 3.34 |
| 1:10 | 0.33 | 4.66 | 5.30 | 4.34 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A synergistic biocidal composition comprising: 2,2-dibromomalonamide and 2,2-dibromo-3-nitrilopropionamide wherein the weight ratio of 2,2-dibromomalonamide to 2,2-dibromo-3-nitrilopropionamide is between about 31:1 and about 1:1.

2. A composition according to claim 1 which is: paint, coating, aqueous emulsion, latex, adhesive, ink, pigment dispersion, household cleaner, industrial cleaner, detergent, dish detergent, mineral slurry, polymer emulsion, caulk, adhesive, tape joint compound, disinfectant, sanitizer, metalworking fluid, construction product, personal care product, textile fluid, industrial process water, oilfield functional fluid, or fuel.

3. A composition according to claim 1 in which the pH is 5 or greater.

4. A method for controlling microorganism growth in an aqueous or water-containing system, the method comprising treating the aqueous or water-containing system with an effective amount of a composition according to claim 1.

5. A method according to claim 4 wherein the aqueous or water-containing system is paint, paint, coating, aqueous emulsion, latex, adhesive, ink, pigment dispersion, household cleaner, industrial cleaner, detergent, dish detergent, mineral slurry, polymer emulsion, caulk, adhesive, tape joint compound, disinfectant, sanitizer, metalworking fluid, construction product, personal care product, textile fluid, industrial process water, oilfield functional fluid, or fuel.

* * * * *